United States Patent
Kang et al.

(10) Patent No.: US 7,806,877 B2
(45) Date of Patent: Oct. 5, 2010

(54) GRIPPABLE PACKET APPLICATOR

(75) Inventors: Alan H. I. Kang, P.O. Box 11207, Honolulu, HI (US) 96828; George E. Darby, Mililani, HI (US)

(73) Assignee: Alan H. I. Kang, Honolulu, HI (US)

( * ) Notice: Subject to any disclaimer, the term of this patent is extended or adjusted under 35 U.S.C. 154(b) by 242 days.

(21) Appl. No.: 11/463,528

(22) Filed: Aug. 9, 2006

(65) Prior Publication Data
US 2008/0039812 A1 Feb. 14, 2008

(51) Int. Cl.
*A61F 13/40* (2006.01)
(52) U.S. Cl. .............. 604/306; 604/3; 206/210; 206/484
(58) Field of Classification Search .......... 604/3, 604/306, 308; 206/210
See application file for complete search history.

(56) References Cited

U.S. PATENT DOCUMENTS

| | | | | |
|---|---|---|---|---|
| 2,629,890 A * | 2/1953 | Di Giovanna | ............. | 15/229.13 |
| 2,964,772 A * | 12/1960 | Crawford | ............. | 15/244.1 |
| 3,053,385 A * | 9/1962 | Spees | ............. | 206/361 |
| 3,196,478 A * | 7/1965 | Baymiller et al. | ............. | 401/132 |
| 3,240,326 A * | 3/1966 | Miller | ............. | 206/361 |
| 3,299,464 A * | 1/1967 | O'Brien et al. | ............. | 15/104.94 |
| 3,315,801 A * | 4/1967 | Lowry | ............. | 206/469 |
| 3,369,267 A * | 2/1968 | Friedland et al. | ............. | 15/104.94 |
| 3,466,131 A * | 9/1969 | Arcudi | ............. | 401/132 |
| 3,635,376 A * | 1/1972 | Hellstrom | ............. | 222/107 |
| 3,635,567 A * | 1/1972 | Richardson, Jr. | ............. | 401/132 |
| 3,636,922 A * | 1/1972 | Ketner | ............. | 118/264 |
| 3,765,595 A * | 10/1973 | Bernhardt | ............. | 229/125.08 |
| 3,826,259 A * | 7/1974 | Bailey | ............. | 604/310 |
| 3,860,348 A * | 1/1975 | Doyle | ............. | 401/6 |
| 4,127,339 A * | 11/1978 | Malacheski et al. | ............. | 401/132 |
| 4,131,195 A * | 12/1978 | Worrell, Sr. | ............. | 206/205 |
| 4,140,409 A * | 2/1979 | DeVries | ............. | 401/132 |
| 4,332,319 A * | 6/1982 | Hurwood | ............. | 206/210 |
| 4,427,115 A * | 1/1984 | Laipply | ............. | 206/484 |
| 4,428,477 A * | 1/1984 | Cristofolo | ............. | 206/210 |
| 4,430,013 A * | 2/1984 | Kaufman | ............. | 401/132 |
| 4,493,574 A * | 1/1985 | Redmond et al. | ............. | 401/132 |
| 4,540,612 A * | 9/1985 | Rhyner | ............. | 428/35.2 |
| 4,596,481 A * | 6/1986 | Tanaka | ............. | 401/132 |
| 4,643,725 A * | 2/1987 | Schlesser et al. | ............. | 604/306 |
| 4,696,393 A * | 9/1987 | Laipply | ............. | 206/210 |
| 4,701,168 A * | 10/1987 | Gammons | ............. | 604/310 |
| 4,796,751 A * | 1/1989 | Madkour | ............. | 206/223 |
| 4,893,956 A * | 1/1990 | Wojcik et al. | ............. | 401/130 |
| 5,320,217 A * | 6/1994 | Lenarz | ............. | 206/209 |
| 5,470,323 A | 11/1995 | Smith | | |
| 5,487,581 A * | 1/1996 | Carmo et al. | ............. | 294/137 |

(Continued)

*Primary Examiner*—Tatyana Zalukaeva
*Assistant Examiner*—Paula L Craig
(74) *Attorney, Agent, or Firm*—Convergent Law Group LLP

(57) ABSTRACT

The invention provides an easily gripped, single use or multiple use, packet applicator that contains, protects, dispenses and applies powders, solids, semi-solids, semi-liquids, and liquids. The packet contents, or "payload", are selected from a wide variety of personal care, domestic, office, commercial, and industrial substances, such as: sunscreen, soap, cosmetics, cosmetics removers, and medicaments for application to epidermis and other body surfaces; detergents, waxes, cleansers, and polishes for application to household surfaces; and lubricants, paints, sensors, and sealants for application to commercial and industrial surfaces. Embodiments of the packet applicator can include a rotatable grip.

15 Claims, 3 Drawing Sheets

U.S. PATENT DOCUMENTS

| | | | |
|---|---|---|---|
| 5,487,932 A * | 1/1996 | Dunshee | 428/68 |
| 5,562,642 A | 10/1996 | Smith | |
| 5,615,440 A * | 4/1997 | Cowan et al. | 15/104.94 |
| 5,771,524 A * | 6/1998 | Woods et al. | 15/209.1 |
| 5,775,826 A * | 7/1998 | Miller | 401/132 |
| 5,957,605 A | 9/1999 | Cohen et al. | |
| 5,961,500 A * | 10/1999 | Weinstein | 604/304 |
| 6,007,264 A * | 12/1999 | Koptis | 401/132 |
| 6,446,795 B1 * | 9/2002 | Allen et al. | 206/210 |
| 6,505,740 B1 * | 1/2003 | Marlin et al. | 206/524.5 |
| 6,892,513 B1 * | 5/2005 | Barr et al. | 53/458 |
| 7,235,250 B2 * | 6/2007 | Padlo et al. | 424/401 |
| 7,552,823 B2 * | 6/2009 | Schuehrer | 206/484 |
| 2004/0237235 A1 | 12/2004 | Visioli et al. | |
| 2005/0058499 A1 * | 3/2005 | Tsaur | 401/132 |
| 2006/0283727 A1 * | 12/2006 | Nelson et al. | 206/219 |

* cited by examiner

GRIPPABLE PACKET APPLICATOR

BACKGROUND OF THE INVENTION

1. Field of the Invention

The invention is directed to an easily gripped, single use or multiple use packet applicator that contains, protects, dispenses and applies powders, solids, semi-solids, semi-liquids, and liquids. More particularly, the invention provides a method of producing and using a packet applicator, and a packet applicator providing greater convenience and less mess in the application of packet contents. The packet contents, or "payload" adsorbed onto adsorbent pads, are selected from a wide variety of personal care, domestic, office, commercial, and industrial substances. Of particular commercial importance are payloads such as sunscreen, soap, cosmetics, cosmetics removers, powders, and medicaments for application to epidermis and other body surfaces and orifices; detergents, waxes, cleansers, and polishes for application to household, office, and commercial surfaces; and lubricants, paints, solvents, sensors, adhesives, abrasives, and sealants for application to commercial and industrial surfaces.

2. Related Art

One of the unsolved problems of self-contained packet applicators, e.g., sunscreen lotion applicators, glue applicators, cleanser applicators, etc., is the lack of an applicator that (i) provides a package with high packing density and long shelf life, (ii) at the time of application is easy to open and use, (iii) does not coat the user's fingers with payload during application, (iv) adapts the adsorbent pad(s) to the nature of the payload, (v) has high storage density, and (vi) is very inexpensive to manufacture. It also desirable that the packet applicator provide multiple uses (desorptions of payload) and does not leak residual payload between initial opening, subsequent uses, and disposal of the applicator.

The term "payload" means herein the substance to be contained in the packet applicator and applied after the packet is opened. Payload may be a powder, solid, semi-solid, semi-liquid, or liquid (including a volatile or semi-volatile liquid). The term "packet applicator" means a device that contains, protects, dispenses, and applies a payload, and optionally can be resealed to prevent leakage of the payload between initial opening of the packet applicator and dispensing of payload. "Dispensing" means desorption of payload from the adsorbent pad(s) of an opened packet applicator and distribution of the desorbed payload on a target surface. The terms "packet", "applicator", and "Kang applicator" hereafter all mean the packet applicator of the invention unless expressly given a different meaning. The term "activated applicator" means an opened packet applicator configured to apply payload. The term "resealed applicator" means a packet applicator that has been previously been opened and thereafter has been resealed for future use or disposal. The term "target surface" means the surface on which a user applies a payload using the applicator (or on which the payload is otherwise deposited, e.g., by evaporation or inhalation). The term "grippability" means the ability of a user to grip one or more surfaces of the applicator in order to open the applicator and to guide the applicator during application of a payload. The term "stray release" means (i) applying payload to any surface other than the intended target surface as well as (ii) payload that leaks from a resealed packet before disposal of the applicator. The term "to package" means to load, contain, and protect a payload in a packet, and, in resealable packets, to also prevent stray release. The term "film" means the planar member in which one or more adsorbent pads (each, an "applicator pad") is sealed before activation; film is typically paper, woven textile, non-woven textile, plastic, metal, and/or a composite thereof; any of the preceding can be coated with plastic on interior and/or exterior packet surfaces to improve impermeability of the film or grippability of the exterior surface of the packet. An applicator pad can be natural fiber, synthetic fiber, yarn, woven textile, non-woven textile, metal (including steel wool and other "metal wools"), composite, or foam, or a combination of two or more such materials; non-abrasive or gently abrasive materials are used to make applicator pads for personal care embodiments, e.g., facial wipes; medium abrasive pads are used to make applicator pads for some household care embodiments, e,g., glass-top range cleaners; very abrasive materials are used to make applicator pads for some industrial embodiments, e.g., rust removers. "Pore size" and "pad pore size" mean the dimensions of the interstices between the fibers, foam walls, or other structural element of an adsorbent pad in the Kang applicator. A "zip strip" means a mating set of linear, small, plastic lips that can be repeatedly engaged and disengaged, e.g., as commonly used in the resealable margin of sandwich bags. The "top" of an applicator means the film surface of an opened Kang applicator. The "bottom" of an applicator means the surface of an opened Kang applicator with the adsorbent pad(s) exposed.

The prior art of packet applicators, such as that of U.S. Pat. No. 5,470,323 (Smith), U.S. Pat. No. 5,562,642 (Smith), and US App. No. 20040237235 (Visioli) includes applicator pads sandwiched between two rectilinear sheets of film in which three of the four margins are peelably sealed, but cannot be resealed. The Smith applicators have no special provision for holding an opened applicator. The Visioli applicator includes embodiments having structural elements of a gusset or strap on one side of an opened applicator to improve a user's ability to hold and control the applicator, but not a handle on the spine or an opened packet. U.S. Pat. No. 5,957,605 (Cohen) provides special purpose opening tabs and a handle on the spine of the opened applicator, but uses six or more structural elements, including opening tabs and an optional handle stiffener, to make the applicator, compared with two structural elements in the basic embodiment of the Kang applicator.

In its simplest embodiment (i.e., that with the fewest structural elements), Cohen's applicator (U.S. Pat. No. 5,957,605, FIG. 4), comprises an impermeable barrier, an adsorbent pad, two opening tabs, a hole for injection of product, and a hole cover. Although Cohen mentions (U.S. Pat. No. 5,957,605, col. 9, ln. 49-55) alternative, reclosable embodiments that include closure devices such as mating dimples, "a Velcro dot" or a "zip strip" on the outer edge of the applicator, all of which add additional structural elements, no detail about resealable embodiments is disclosed or whether reclosure of the Cohen applicator prevents liquids from leaking from the applicator. The technical problem addressed by Cohen is a multipurpose applicator that is separately manufactured and stockpiled "empty", then filled with various products in response to product orders. All embodiments of Cohen's applicator have a bulky, complex structure, e.g., a separate outer covering (referred to as a "label" in Cohen), an impermeable barrier (replaced by a label alone in FIG. 4 of Cohen), a product injection aperture, a product dispensing aperture in the impermeable barrier, a thick, full-length adsorbent pad, a handle formed around a reservoir or a stiffener, and opening tabs, and require complex manufacturing compared to the Kang applicator. Cohen introduces significant complexity of applicator structure in exchange for enabling a manufacturer to defer a decision about what product to load in the applicator. Most embodiments of Cohen's applicator have both a label and an impermeable film; a label is typically applied to the exterior of the impermeable film of a generic applicator after the manufacturer decides what payload to insert into the generic applicator. Neither Visioli nor Cohen disclose adapting the characteristics of the adsorbent pad to the nature of the payload. Varying the adsorbent pad characteristics in Cohen's applicator conflicts with Cohen's design limitation of making a generic applicator for which a payload is later selected and injected. The bulky reservoirs and full-length pad of Cohen's applicator greatly reduce the number of applicators that can be stored in a given volume (the number of applicators that can be stored in a given volume is called herein, "storage density").

The technical problem to be solved is to provide an applicator that (1) packages, dispenses, and applies a variety of payloads, (2) is usable for single or multiple applications, (3) is easy to open and use without stray release, (4) adapts the adsorbent pad(s) to the nature of the payload, (5) has high storage density, and (6) is very inexpensive to manufacture. There is unmet demand for such an applicator in the sectors of pharmaceuticals, personal care, cosmetics, cleaning, painting, adhesives, abrasives, and lubrication.

SUMMARY OF THE INVENTION

The instant invention, called herein the "Kang applicator," comprises one or two payload-containing, adsorbent pads, each attached on one side to, and sandwiched between, a folded, typically rectilinear sheet of film. The folded film is preferably made of plastic, metallic, or plastic-coated metallic material. Three of the four margins around the perimeter of the folded sheet are peelably sealed and the fourth, non-peelably sealed, typically wider margin forms a "main grip" or, simply, "grip", in which the film of the fourth margin is adhered together or is otherwise essentially solid. The margin opposite the grip is not completely sealed at the very edge (each such margin opposite the grip is called an "opening edge" of the Kang applicator); the opening edges permit a user to grasp the opening edges, to peel back the folded sheet to expose the applicator pad(s), and to dispense the payload by grasping the grip and pressing the adhesive pad(s) of the applicator against a target surface. The sheet of film is preferably manufactured to be stiff, even very stiff, except in the areas of the peelable margins and of a "hinge line" along the base of the grip. The "base" of the grip is the part of the grip closest to the edge of the adsorbent pad(s). The hinge line allows the "wings" of the peeled-open, folded sheet to rotate easily to expose the adhesive pad(s) for use. The "grip" is the very stiff, non-peelably sealed margin between the hinge line and the non-peelable edge of the packet. The sheet margins that form the grip and the opening edges of the applicator can be waffled, dimpled, or have other treatment to improve grippability. Optionally, the grip can be coated with a "sticky feeling" elastomer that further improves grippability of the applicator. Alternative embodiments of the invention can be resealed with a "zip strip" embedded in, or with a bead of tacky elastomer deposited along, the three sheet margins other than the grip.

The Kang applicator can be used to package payloads such as: gels, ointments, salves, lotions, cosmetics, and other pharmaceutical and personal care payloads; detergents, surfactants, abrasives, and other payloads for cleaning; paints, sealers, and other payloads for painting; and grease, oil, and other payloads for lubrication. The Kang applicator (1) packages and dispenses a variety of payloads, (2) is usable for single or, a resealable embodiment, multiple applications of payload, (3) is easy to open and use without stray release, (4) adapts the adsorbent pad(s) to the nature of the payload, (5) has high storage density, and (6) can be manufactured very inexpensively.

DETAILED DESCRIPTION OF THE PREFERRED EMBODIMENTS

Figure 1:
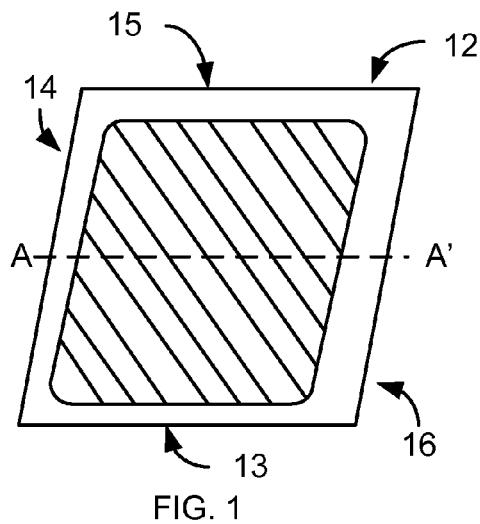
FIG. 1 shows a top perspective view of an unopened, one-pad Kang applicator.
Figure 2:
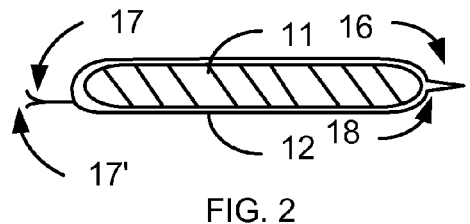
FIG. 2 shows a longitudinal cross-section of FIG. 1 along axis A-A' of FIG. 1.

As shown in FIGS. 1 and 2, the basic embodiment of a Kang applicator comprises a single adsorbent pad (11) attached on one side to, and sandwiched between, a folded, sheet of film (12). The applicator is shown unopened in FIG. 1. The adsorbent pad (11) is affixed to the film (12) using adhesives, heat fusion, or other methods known in the art. The adsorbent pad may be woven or non-woven, natural or synthetic, textile or other pliable, adsorbent material (including without limitation, open cell foam, and carbon fiber, metal, or composite wools) known in the art. The adsorbent pad material and method of attachment to the sheet of film are selected to be compatible with the payload and with the target surface. For instance, if the pad is affixed to the film using adhesive, the payload must not react with the adhesive to detach the pad. If the target surface of the pad is human skin, the adsorbent pad material must have a tactile quality acceptable to users.

Figure 7:
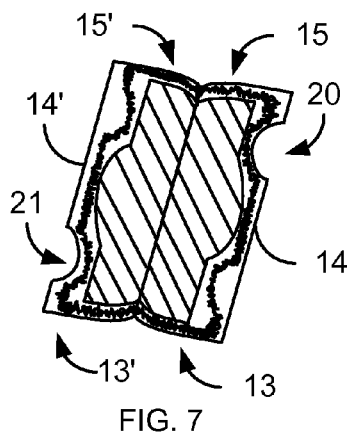
FIG. 7 shows a perspective of a partially opened two-pad Kang applicator with offset indentations on the opening edges.
Figure 8:
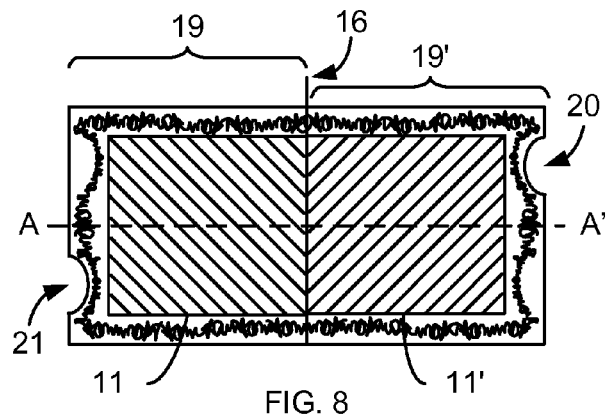
FIG. 8 shows a bottom view of an opened, two-pad Kang applicator with offset indentations on the opening edges.

Three margins (13, 14, and 15) of the four margins around the perimeter of the folded sheet are peelably sealed and the fourth, preferably wider, non-peelably sealed margin (16) forms a "grip". The film of the fourth margin is adhered or heat-fused together to create a stiffer grip; the fourth margin can also be manufactured as a solid, e.g., by thermoplastic extrusion of the film with a preformed grip. The grip, whether created by the fold of the film or by extrusion, can be additionally stiffened and/or its grippability improved by deposition of suitable layer of plastic on the grip surface. The margin (14) opposite the grip (16) is not completely sealed at the very edge so that such the edge of such margin (14), called the "opening edge" (17, 17'), can be gripped by a user to peel open the packet applicator. Each opening edge can be made with indentation to facilitate a user's gripping the other opening edge; the indentations are offset, as shown in FIGS. 7 and 8. If made of plastic, the sheet of film can comprise at least one layer of polymer selected from the group consisting of polyamides; polyolefins; polyesters; polyethylene vinyl alcohol; polyvinylidene chloride, anhydride-modified ethylene homopolymer, anhydride-modified ethylene copolymer, and combinations thereof. Alternate embodiments of the opening edge can include a tear string or tear path (i.e., a notched or weakened lateral path across the opening edge of the packet that opens the packet when torn along the path), especially for nonresealable embodiments; in such embodiments, the opening edges can be completely sealed.

FIG. 2 is a longitudinal cross-section along axis A-A' of an unopened, single pad, Kang applicator. The reference numerals in the description of FIG. 1 also apply to FIG. 2. The structural simplicity of the Kang applicator makes it very inexpensive to manufacture in high volumes. The ease of manufacturing a Kang applicator is self-evident: adsorbent pads are adhered, heat-fused, chemically bonded, or otherwise affixed to a strip of film running in a fabrication line, a payload appropriate for the type of affixed adsorbent pad is loaded on the adsorbent pads, the strip of film is severed between the opening edge boundaries, each packet folded at the main grip, and the peelably sealed edges are sealed. The structural simplicity and integral grip of the Kang applicator also provide very high storage densities that are essentially equal to the storage densities of packet applicators without grips.

Figure 3:
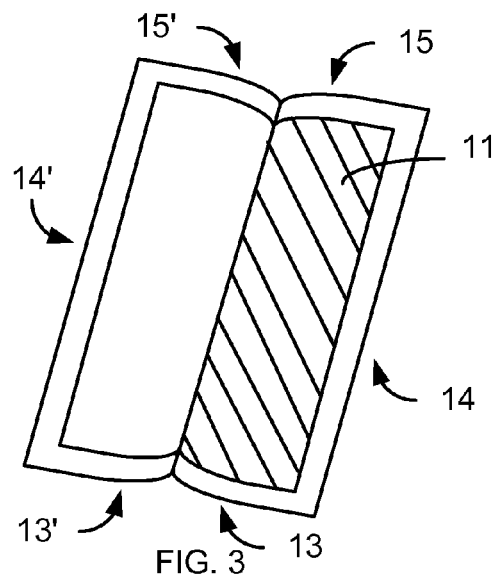
FIG. 3 shows a perspective of a partially opened one-pad Kang applicator.

As shown in FIG. 3, peeling open the folded sheet of film exposes the applicator pad for use. Opening the Kang applicator is the process of separating a first set of three peelable margins, 13, 14, and 15, from the set of counterpart margins 13', 14', and 15'. Each margin other than the grip is called a "peelable margin". The "longitudinal" axis (A, A' in FIG. 5) of a Kang applicator bisects the grip. The ability to seal, peel, and optionally reseal, the three, peelable margins can be provided by the use of adhesives (e.g., a sticky elastomer), an embedded "zip strip", or other means, as explained below. The sheet of film is preferably manufactured to be somewhat flexible for embodiments for personal care uses, to very stiff for embodiments are for abrasive uses, except in the areas of the peelable margins and of a "hinge line" (18) along the base of the grip, as shown in FIGS. 1 and 6. The portion of the sheet between an opening edge and the hinge line is called a "wing" (19, 19'). The grip (16) is the non-peelably sealed margin between the hinge line (18) and the non-peelable edge of the packet. To enhance the ability of each wing to pivot on the hinge line, the hinge line may optionally be creased or of reduced thickness.

Figure 4:
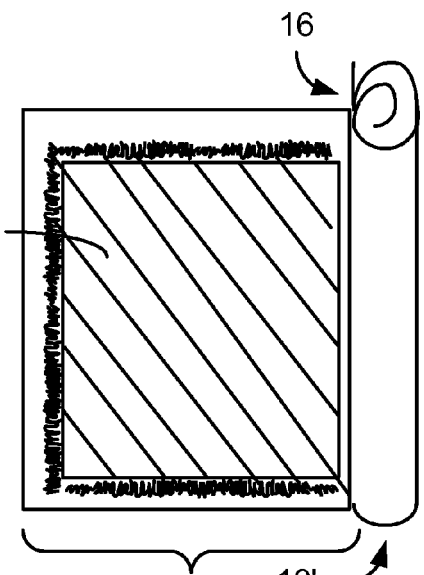
FIG. 4 shows a bottom view of an opened, one-pad Kang applicator with the pad-less wing curled back.

As shown in FIG. 4, when the applicator has been opened, each wing pivots on the hinge line, which exposes the adhesive pad for use. Greater stiffness of the film to which an adsorbent pad is attached, and of the grip, allows the user to better modulate the pressure on the adsorbent pad when applied and moved against a target surface. A stiff grip distributes pressure applied to the grip more uniformly across the lateral aspect of the pad. Stiff film behind the pad distributes pressure applied to the pad more uniformly across the area of the pad. Higher pressure of an adsorbent pad against a target surface typically desorbs from the pad and applies to the target surface increased amounts of payload.

For economy of manufacture, including the ability to provide resilience and variable amounts of stiffness in various portions of the sheet of film, the sheet of film is preferably made of plastic. The sheet of film can alternatively be made of metallic, or plastic-coated metallic, material. The choice of film material depends primarily upon the desired stiffness and resilience of the film, manufacturing economics, and shelf-life, reactivity, and permeability of the payload. Other structural materials, e.g., coated paper, are possible, but such other materials are typically inferior in the performance criteria recited in the preceding sentence compared with the preferred and alternate materials. In a one-pad embodiment of the Kang applicator, if stiffness and resilience are not required to survive conditions of storage and distribution, the more pliable the wing without an adsorbent pad, the better, since after opening, that wing can curl back, out of the way, during application, as shown in FIG. 4. Resilience of the film material is typically selected so that the packet is not accidentally punctured during expected handling before use. Selection of film material based on stiffness and resilience of the film, manufacturing economics, and shelf-life, reactivity, and permeability of the payload is well known in the art.

The sheet margins that form the grip and the opening edges of the applicator can be waffled, dimpled, or have other treatment to improve grippability. The grip, opening edges, and/or the exterior side of the film to which a pad is attached can optionally be coated with a "sticky" elastomer that further improves grippability. To apply payload after opening a single-pad applicator, a user typically grips the grip between the thumb and index finger of one hand, and presses the sheet behind the adsorbent pad using the phalangeal areas of the remaining fingers of that hand, thereby causing the adsorbent pad to contact a target surface and to desorb payload onto the target surface.

Figure 5:
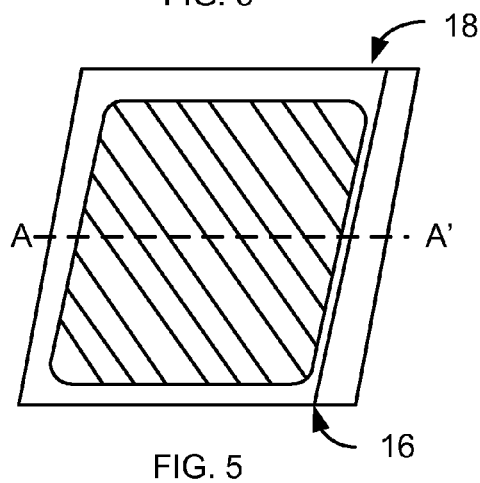
FIG. 5 shows a top perspective view of an unopened, two-pad Kang applicator.
Figure 6:
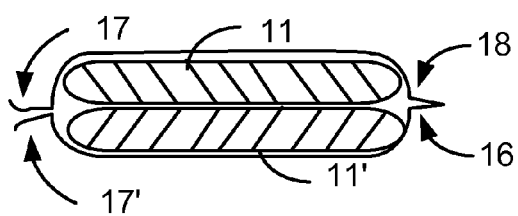
FIG. 6 shows a longitudinal cross-section of FIG. 5 along axis A-A' of FIG. 5.

As shown in FIGS. 5 and 6, a basic two-pad embodiment of a Kang applicator comprises an adsorbent pad (11, 11') attached to the interior (bottom) surface of each wing, and sandwiched between a folded, sheet of film. The applicator is shown unopened in FIG. 5. The description above of a one-pad embodiment of the Kang applicator applies with equal force to a two-pad embodiment of the Kang applicator, except that an adsorbent pad is mounted on the interior surface of each wing, as shown in FIGS. 5 to 10, and the film of each wing has adequate stiffness and resilience to better modulate the pressure on the adsorbent pad when applied against a target surface.

FIG. 6 is a longitudinal cross-section of an unopened, two-pad, Kang applicator.

As shown in FIG. 7, peeling open the folded sheet exposes the applicator pads for use. Like the one-pad embodiment, the two-pad embodiment has three peelable margins (13 and 13', 14 and 14', and 15 and 15') and a fourth, preferably wider, non-peelably sealed margin that forms the grip. The margin (14, 14') opposite the grip (16) is not completely sealed at the very edge so that the edge of such margin (14, 14') forms an opening edge (17, 17'); the opening edges are gripped and pulled by a user to peel open the two-pad embodiment of the Kang applicator. The ability to seal, peel, and optionally reseal, the three, peelable margins can be provided by the use of adhesives, an embedded "zip strip", or other means, as explained below. The opening edges can optionally have offset indentations (20, 21). The sheet of film is preferably manufactured to be stiff, even very stiff, except in the areas of the peelable margins and of a "hinge line" (18) along the base of the grip. As in the one-pad embodiment, the portion of the sheet between an opening edge and the hinge line is called a "wing" and the grip (16) is the non-peelably sealed margin between the hinge line (18) and the non-peelable edge of the packet. To enhance the ability of each wing to pivot on the hinge line, the hinge line may optionally be creased or of reduced thickness. Alternate embodiments may use a tear string or tear path, as discussed above, as a means of opening a packet. By placing the tear string or tear path on the opening edge side of a resealing means (zip strip, sticky elastomer, etc.), a resealable packet is provided; however, a tear string adds a structural element, and grippable opening edges are easier for users to manipulate, especially if the film of the packet is stiffer (harder to tear), than a tear path; therefore, opening edges are the preferred means for opening a packet.

As shown in FIG. 8, when the applicator has been opened, each wing (19, 19') pivots on the hinge line, which exposes both adhesive pads for use. Greater stiffness of the film to which each adsorbent pad is attached, and of the grip, allows the user to better modulate the pressure on the adsorbent pads when applied against a target surface. A stiff grip distributes pressure applied to the grip more uniformly across the lateral aspect of the pads. Stiff film behind the pads distributes pressure applied to the pad more uniformly across the area of the pad. Higher pressure of the adsorbent pads against a target surface typically desorbs from the pads and applies to the target surface increased amounts of payload.

For economy of manufacture, including the ability to provide resilience and variable amounts of stiffness in various portions of the sheet of film, the sheet of film in a two-pad embodiment is also preferably made of plastic. The sheet of film can alternatively be made of metallic, or plastic-coated metallic, material. The choice of film material depends primarily upon the desired stiffness and resilience of the film, manufacturing economics, and shelf-life, reactivity, and permeability of the payload. Resilience of the film material is typically selected so that the packet is not accidentally punctured during expected handling before use. Selection of film material based on stiffness and resilience of the film, manufacturing economics, and shelf-life, reactivity, and permeability of the payload is well known in the art.

The sheet margins that form the grip and the opening edges of the applicator can be waffled, dimpled, or have other treatment to improve grippability. The grip, opening edges, and/or the exterior (top) side of the film can optionally be coated with a "sticky" elastomer that further improves grippability.

As shown in FIG. 8, the peelable seal (22) of the opening edges, especially on larger Kang applicators, can be contoured to form one or more, indented, opening edges and the remainder of that margin configured without an opening edge. The adsorbent pad(s) can be contoured around such opening edges, which maximizes the area of the adsorbent pad(s).

Figure 9:
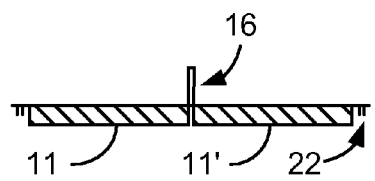
FIG. 9 shows a side view of an opened, two-pad Kang applicator along axis A-A' of FIG. 8.

FIG. 9 shows a side view of an opened, two-pad Kang applicator. To apply payload after opening a two-pad applicator, a user typically grips the grip (16) between the index finger and middle finger of one hand, and presses the sheet behind one adsorbent pad using the thumb, and the sheet behind the other adsorbent pad using the phalangeal areas of the remaining fingers, of that hand, thereby causing the adsorbent pads to contact a target surface and to desorb payload onto the target surface.

In all embodiments of the Kang applicator, during application of payload to a target surface, the user's hand is shielded from the payload by the sheet of film. The wider and thicker the grip (16) is, typically up to approximately 3 cm wide and 3 mm thick, the easier the applicator is to grip and use without compromising cost of production and storage density. For storage, a wide grip can be folded at the hinge line to lie against a wing of the unopened packet. The dimensions and stiffness of the grip, and stiffness of the sheet of film, are selected based on distribution constraints (e.g., storage space), intended use (e.g., household goods, first aid kit, commercial uses), pressure to be applied (e.g., cosmetics application, rust removal), and dexterity of intended user (e.g., normal hands, arthritic hands).

The dimensions of the Kang applicator primarily reflect the area and topology of the target surface. A large target surface, e.g., a kitchen window to be cleaned, would typically be paired with a two-pad Kang applicator with wings (and pads) that are each several square inches in area. A small target area, e.g., a user's nares that are to receive a payload of inhalable antiasthma powder, would typically be paired with a two-pad Kang applicator that opens to the width of the user's nostrils. A two-pad Kang applicator for painting might be eight inches wide when opened, but a one-pad Kang applicator for acne medicine might be a half-inch wide when opened.

In all embodiments of the Kang applicator, the payload is adsorbed or otherwise placed (e.g., for semisolid and solid payloads) on the adsorbent pad(s) in a Kang applicator at the time of manufacture and before sealing of the peelable margins. Adsorption or placement of the payload on the adsorbent pad(s) of the packet during manufacturing of the Kang applicator is called "loading" the packet. Soon after, typically immediately after, loading of a packet the peelable margins are sealed. Sealing of a packet is typically least expensively done using heat fusing or using adhesive applied to one or both interior surfaces of the areas of the folded sheet of film that form the peelable margins. The strength of the seal formed in the peelable margins can be improved by using waffling or dimpling A means can be included to reseal the peelable margins of the applicator after a given use (initial or subsequent). The preferred means for resealing is a "zip strip" embedded in the three peelable margins.

Figure 10:
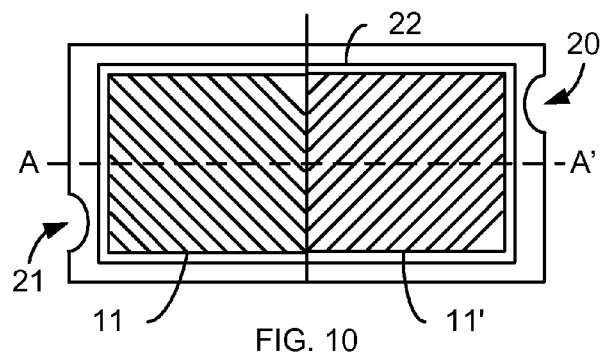
FIG. 10 shows a bottom view of an opened, two-pad Kang applicator with a zip strip in the peelable margins.
Figure 11:
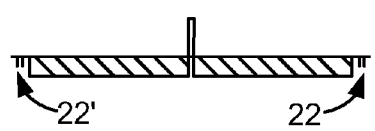
FIG. 11 shows a longitudinal cross-section of FIG. 10 along axis A-A' of FIG. 10.

As shown in FIGS. 10 and 11, mating segments (22, 22') of a zip strip can be formed in the peelable margins of a packet. In embodiments of the applicator that have zip strips, adhesive may also be placed in the peelable margins as part of loading and sealing the packet. The selection of whether to omit adhesive in the peelable margins in embodiments of the packet with a zip strip, or to use adhesive in addition to a zip strip, depends principally on the value, volatility, and reactivity of the payload, and the typical time elapsed between manufacture of the packet. The greater the value, volatility, and reactivity of the payload, or the typical time elapsed between manufacture of the packet and opening of the packet for use, the greater the benefit from using both a zip strip and adhesive. Peelable adhesives are well known in the art. Resealing a zip strip allows the Kang applicator to be resealed after an initial use, thereby permitting one or more subsequent openings of the applicator and applications of payload to target surfaces. Resealing a zip strip also prevents stray release before disposal of the applicator.

The grip is typically formed by joining, by use of adhesive and/or heat fusion, with or without waffling or dimpling, and with or without an additional layer of stiffening plastic, the portions of the folded sheet between the hinge line the and fold. The hinge line and grip are impermeable to payload.

Figure 12:
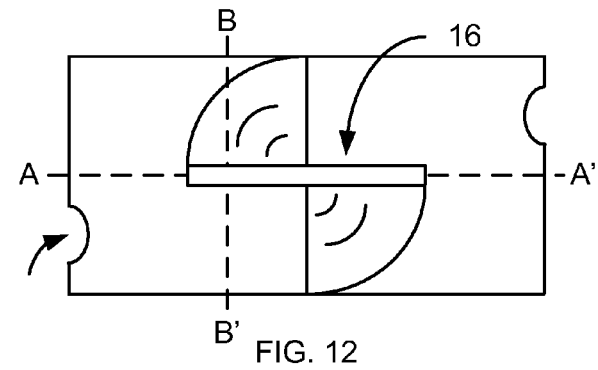
FIG. 12 shows a top view of a rotated grip on an opened two-pad Kang applicator.
Figure 13:
FIG. 13 shows lateral cross section along axis A-A' of FIG. 12.
Figure 14:
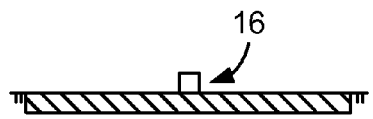
FIG. 14 shows lateral cross section along axis B-B' of FIG. 12.

As shown in FIGS. 12, 13, and 14, in an alternate embodiment primarily for use in Kang applicators with two adsorbent pads, the material in the grip (16) in the area along the hinge line is selected to be distensible so that, after the packet is opened, the grip (called in this embodiment a "rotatable grip") can be rotated from alignment with the lateral axis of the opened applicator to alignment with the longitudinal axis of the opened applicator. FIG. 12 shows a top view of a rotatable grip, after rotation, on an opened two-pad Kang applicator. FIG. 13 shows lateral cross section along axis A-A' of FIG. 12. FIG. 14 shows lateral cross section along axis B-B' of FIG. 12. Alignment of the grip with the longitudinal axis of the opened applicator permits pressure to be applied by the grip across the midsection of each adhesive pad. This rotatable grip embodiment is particularly useful when maximum pressure is to be exerted to press the adsorbent pads against a target surface.

The strength, abrasiveness, and depth of the adsorbent pad in a Kang applicator are selected for the intended use. The pore size and rigidity of the adsorbent pad(s) in a Kang applicator primarily reflect the payload viscosity if a liquid payload, particle size if a powdered payload, or resilience if solid payload, as well as the desired rate of desorption and abrasive force to be applied to a target surface. For example, a pad for a Kang applicator for cosmetics use would typically be soft, thin, and non-abrasive. To package a viscous payload, such as sunscreen, the pore size of each of the one or more applicator pads in a Kang applicator is preferably larger than the pore size used to package a non-viscous payload, such as a facial cleaner. A pad for a Kang applicator with a payload of solvent to remove contaminants before painting primer on a metal surface would typically be thick, rigid, and abrasive. Non-woven pad material can be selected from the group consisting of thermoplastic polymeric fiber, cellulosic fiber, and combinations thereof. If thermoplastic polymeric fiber is used, it can be selected from the group consisting of polyolefins, polyamides, and polyesters. The selection of adsorbent pad material for a given payload and target surface is known in the art.

Although the folded sheet of film in a Kang applicator is typically rectangular before folding of the sheet during manufacturing, other shapes may be used, e.g., circular, oval, hexagonal, etc. For personal care products, unusual shapes sometimes improve sales.

Thickness of the sheet of film other than in the peelable margins and hinge line may not be uniform. The thickness and geometry of reinforcement reflects the payload and intended use of a given Kang applicator. For instance, a Kang applicator for use with cosmetics may use a slightly concave web of reinforcement radiating from a point in a wing aligned behind the centerpoint of a pad; a slight concave web of reinforcement would provide a springier feel than a uniformly stiff, flat reinforcement.

In a two-pad Kang applicator, the edges of the pads nearest the hinge line can substantially abut each other so that, when the Kang applicator is opened, there is little or no space between the pads. Alternatively, a single adsorbent pad that spans the width of both wings (less the peelable margins) when opened can be affixed to the interior surface of the wings, but typically made thinner at the hinge line to facilitate folding at the hinge line during manufacturing. In an alternative embodiment of a two-pad Kang applicator, each pad can have a different abrasiveness, shape, or other characteristic. For example, one pad could have a rougher texture for initial abrasion of a target surface, and the other a smoother texture for polishing the target surface.

Figure 15:
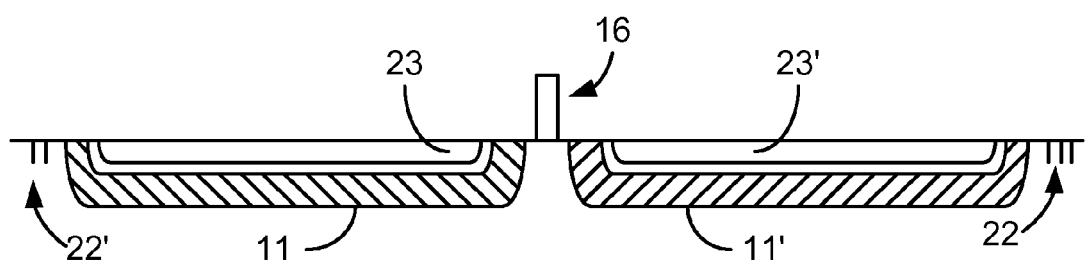
FIG. 15 shows longitudinal cross-section of an opened, two-pad Kang applicator that contains a rupturable bladder and uses a peelably sealable zip strip.

As shown in FIG. 15, alternate embodiments of the Kang applicator can contain a bladder that can be ruptured just prior to opening. FIG. 15 shows longitudinal cross-section of an opened, two-pad Kang applicator that contains a rupturable bladder and uses a peelably sealable zip strip (22, 22'). The rupturable bladder (23, 23'), filled with a payload, is placed in the packet during manufacturing of the packet. The preferred bladder is one of substantially the same shape as the pad(s) in the packet, but is of smaller area than the pad (11 or 11') covering it, and is placed between the pad(s) and the sheet of film (12) to which a given pad is attached so that, when the bladder is ruptured, the contents of the bladder is adsorbed on the pad and then desorbed on a target surface. The larger area of an adsorbent pad covers a rupturable bladder, and the margin of the adsorbent pad is secured to the film. When the bladder is ruptured, the discharge of a ruptured bladder must flow through the adsorbent pad covering the bladder. The bladder can be adhered to the film, or simply held in place by the adsorbent pad covering it. The bladder can be the only source of payload in a Kang applicator, or can be the source of a second payload that reacts with a first payload already adsorbed on the pad(s). Rupturable bladders are recommended if a Kang applicator is intended to have an extended shelf-life and the payload is volatile. Rupturable bladders are also recommended if a first payload on the pad in contact with a second payload from the bladder will eventually degrade either the first payload on the pad and/or the packet structural elements (sheet of film, pad(s), and adhesive(s)). Containing one payload in a rupturable bladder isolates the two payloads from one another and prevents the degradation. More than one bladder can be included in a Kang applicator. The second and additional bladders are preferably stacked, sandwich style, between the adsorbent pad(s) and the sheet of film to which a given pad is attached.

The Kang applicator can be used to package powdered, solid, semi-solid, semi-liquid, and liquid payloads, such as: gels, ointments, salves, lotions, cosmetics, cosmetics removers, soap, anti-acne medicine, skin lotions, sun block, self-tanning lotion, hair dye, moisturizing lotion, nail polish remover, facial cleanser, powders, cologne, perfume, topical lotions, baby wipes, baby powder, insect bite medication, insect repellant, eye black, ski wax, hand cleaner, and other personal care, recreational activity, and sports payloads; inhalant powder, volatile inhalants, medicaments, pharmaceuticals, and other medicinal payloads; fly wipe, hoof black, insecticide, and other veterinary products; detergents, waxes, oils, surfactants, solvents, abrasives, disposable pot scrubbers, non-stick liquids, and other payloads for cleaning and household uses; paints, abrasives, sealers, stains, adhesives, and other payloads for home, office, commercial, and industrial use; and grease, oil, and other payloads for lubrication.

We claim:

1. A packet applicator comprising:

at least one payload-containing, adsorbent pad;

a folded sheet of film, each of the at least one adsorbent pad being attached on one side to and sandwiched between the folded sheet of film, the folded sheet of film having a perimeter and a plurality of margins at the perimeter, wherein all but at least one of the plurality of margins at the perimeter of the folded sheet of film are peelably sealed, and wherein the at least one of the plurality of margins is wider than a remaining portion of the plurality of margins and non-peelably sealed, the at least one of the plurality of margins forming a grip for holding the packet applicator during use, the folded sheet of film having a reduced thickness along the base of the grip forming a hinge line along the base of the grip, the folded sheet of film including a lateral axis and a longitudinal axis when the packet applicator is opened, a portion of the folded sheet of film in the grip in the area along the hinge line being configured to be rotated from alignment with the lateral axis of the opened applicator to alignment with the longitudinal axis of the opened applicator; and a rupturable bladder containing a payload, the rupturable bladder residing between the at least one adsorbent pad and a portion of the folded sheet of film to which the at least one adsorbent pad is attached.

2. The packet applicator of claim 1, wherein the folded sheet of film includes at least one of paper, plastic, metal, composite, plastic-coated paper, plastic-coated composite, or plastic coated metal.

3. The packet applicator of claim 1, wherein an opposing margin of the plurality of margins opposite to the grip includes an edge, the edge being incompletely sealed, thereby forming an opening edge.

4. The packet applicator of claim 1, wherein the plurality of margins includes at least one of (1) waffling, (2) dimples and (3) coating with a sticky feeling elastomer.

5. The packet applicator of claim 1, wherein the all but one of the plurality of margins that are peelably sealed are resealable and include including at least one of a zip strip, adhesive, and tacky elastomer.

6. The packet applicator of claim 1, wherein the at least one adsorbent pad includes a pore size and a pad material, the pore size and the pad material being adapted for a payload to be applied to an epidermis.

7. The packet applicator of claim 6 wherein the payload includes at least one of gels, ointments, salves, lotions, cosmetics, cosmetics removers, soap, anti-acne medicine, skin lotions, sun block, self-tanning lotion, hair dye, moisturizers, nail polish remover, facial cleanser, powders, cologne, perfume, insect repellant, eye black, ski wax, and hand cleaner.

8. The packet applicator of claim 1, wherein the at least one adsorbent pad includes a pore size and a pad material, and the pore size and the pad material are adapted for payloads to be applied to household surfaces.

9. The packet applicator of claim 1, wherein the at least one adsorbent pad includes a pore size and a pad material, and the pore size and the pad material are adapted for payloads to be applied to commercial and industrial surfaces.

10. The packet applicator of claim 1, wherein the at least one adsorbent pad includes an additional payload adsorbed to the at least one adsorbent pad, the payload in the rupturable bladder being different from the additional payload.

11. The packet applicator of claim 1, wherein the folded sheet of film includes a lateral axis and a longitudinal axis when the packet applicator is opened, and wherein a portion of the folded sheet of film proximate to the grip in the area along the hinge line is distensible so that, after the packet applicator is opened the grip can be rotated from alignment with the lateral axis of the opened applicator to alignment with the longitudinal axis of the opened applicator.

12. The packet applicator of claim 1, wherein the film includes at least one layer of polymer selected from the group consisting of polyamides, polyolefins, polyesters, polyethylene vinyl alcohol, polyvinylidene chloride, anhydride-modified ethylene homopolymer, anhydride-modified ethylene copolymer, and combinations thereof.

13. The packet applicator of claim 1, wherein the at least one adsorbent pad comprises at least one material selected from the group consisting of natural fiber, synthetic fiber, yarn, woven textile, non-woven textile, metal wool, composite, or foam.

14. The packet applicator of claim 1 wherein the grip is stiffer than the remaining portion of the plurality of margins.

15. The packet applicator of claim 1 wherein the longitudinal axis is perpendicular to the lateral axis.

* * * * *